United States Patent
Nishimura (10) Patent No.: US 11,939,208 B2
(45) Date of Patent: Mar. 26, 2024

(54) LIQUID SUCTION/DISCHARGE DEVICE

(71) Applicant: SHIBUYA CORPORATION, Kanazawa (JP)

(72) Inventor: Noriaki Nishimura, Kanazawa (JP)

(73) Assignee: SHIBUYA CORPORATION, Kanazawa (JP)

(*) Notice: Subject to any disclaimer, the term of this patent is extended or adjusted under 35 U.S.C. 154(b) by 305 days.

(21) Appl. No.: 17/352,804

(22) Filed: Jun. 21, 2021

(65) Prior Publication Data
US 2021/0403313 A1  Dec. 30, 2021

(30) Foreign Application Priority Data
Jun. 29, 2020 (JP) ................................ 2020-112137

(51) Int. Cl.
| | | |
|---|---|---|
| G01N 35/10 | (2006.01) | |
| B67D 7/02 | (2010.01) | |
| B67D 7/42 | (2010.01) | |

(52) U.S. Cl.
CPC ............ *B67D 7/42* (2013.01); *B67D 7/0283* (2013.01); *G01N 35/1011* (2013.01); *G01N 35/1065* (2013.01)

(58) Field of Classification Search
None
See application file for complete search history.

(56) References Cited

U.S. PATENT DOCUMENTS

| | | | | |
|---|---|---|---|---|
| 4,874,114 A | * | 10/1989 | Guigan | G01F 11/10 141/34 |
| 4,916,089 A | * | 4/1990 | Van Suchtelen | B01L 3/0289 117/957 |
| 5,335,481 A | * | 8/1994 | Ward | B65B 23/22 422/933 |
| 5,770,159 A | * | 6/1998 | Marteau D'Autry | B01L 3/0234 422/515 |
| 5,941,636 A | * | 8/1999 | Lu | B01F 35/4111 366/249 |
| 6,101,946 A | * | 8/2000 | Martinsky | B01L 3/0244 422/50 |
| 6,269,846 B1 | * | 8/2001 | Overbeck | G02B 21/0072 427/256 |

(Continued)

FOREIGN PATENT DOCUMENTS

| | | |
|---|---|---|
| JP | 3413418 B2 | 9/1994 |
| JP | 2003302411 A | 10/2003 |
| JP | 4962213 B2 | 3/2009 |

*Primary Examiner* — Brian R Gordon
(74) *Attorney, Agent, or Firm* — FLYNN THIEL, P.C.

(57) ABSTRACT

A liquid is efficiently suctioned and discharged from and to a container formed by a plurality of aligned storing portions for storing the liquid, using a plurality of nozzles. Provided is a liquid suction/discharge device including a container support device for supporting a culture container formed by a plurality of aligned storing portions, and a nozzle support device for supporting a plurality of nozzles in a state in which distal ends of the nozzles are directed downward. The nozzle support device includes a nozzle support member that swingably supports the plurality of nozzles using prescribed parts as support points, and the liquid suction/discharge device further includes a nozzle inclination device for causing each of the nozzles to be inclined with respect to the nozzle support member.

1 Claim, 6 Drawing Sheets

(56) References Cited

U.S. PATENT DOCUMENTS

| | | | | |
|---|---|---|---|---|
| 6,409,971 B1* | 6/2002 | Wilkinson | .......... | B01L 3/50825 |
| | | | | 422/537 |
| 6,599,479 B1* | 7/2003 | Kietzmann | .......... | B01L 3/0268 |
| | | | | 73/864.31 |
| 7,695,682 B2* | 4/2010 | Chojnacki | .............. | G01N 35/10 |
| | | | | 422/561 |
| 8,679,421 B2* | 3/2014 | Sano | ...................... | G01N 35/10 |
| | | | | 422/511 |
| 8,765,079 B2* | 7/2014 | Tokumaru | .............. | C12M 23/10 |
| | | | | 422/566 |
| 9,146,249 B2* | 9/2015 | Buffiere | .................... | B65B 3/04 |
| 2003/0166263 A1* | 9/2003 | Haushalter | ............. | B82Y 10/00 |
| | | | | 346/78 |
| 2007/0122312 A1* | 5/2007 | Chojnacki | .............. | G01N 35/10 |
| | | | | 422/561 |
| 2009/0233816 A1* | 9/2009 | Aoki | .................... | B01L 3/0268 |
| | | | | 506/40 |
| 2012/0156098 A1* | 6/2012 | Sano | ...................... | G01N 35/10 |
| | | | | 422/522 |
| 2013/0017127 A1* | 1/2013 | Tokumaru | .............. | C12M 23/10 |
| | | | | 422/509 |
| 2017/0131314 A1* | 5/2017 | Bachmann | ........ | G01N 35/1009 |
| 2018/0238923 A1* | 8/2018 | Abe | ...................... | B25J 9/1679 |
| 2019/0193272 A1* | 6/2019 | Iwasaki | ................ | B01L 3/0286 |
| 2019/0195905 A1* | 6/2019 | Iwasaki | ................ | B01L 3/0275 |
| 2019/0314808 A1* | 10/2019 | Wilmer | .................... | B01L 3/0275 |
| 2022/0276271 A1* | 9/2022 | Okada | ................ | B25J 15/0616 |

\* cited by examiner

LIQUID SUCTION/DISCHARGE DEVICE

FIELD OF THE INVENTION

The present invention relates to a liquid suction/discharge device and specifically to a liquid suction/discharge device adapted to suction and discharge a liquid from and to a container formed by a plurality of aligned storing portions for storing the liquid, using a plurality of nozzles.

DESCRIPTION OF THE RELATED ART

In the related art, containers formed by a plurality of aligned storing portions for storing liquids are used to culture cells, and for example, operations of suctioning culture liquids from the storing portions where cells and culture liquids are stored and discharging the suctioned culture liquids to the storing portions again are performed.

Although such operations of suctioning and discharging liquids from and to containers for culture are manually performed by operators using tools such as pipettes, it is necessary to culture more cells in a case in which the cultured cells and the like are used for treatment in recent regenerative medicine, and an efficient liquid suction/discharge device has been required for an automatic culture device that automatically performs these culture operations.

As devices that suction or discharge liquids as described above, devices configured to suction or discharge liquids at the same time from a plurality of wells (storing portions) to containers, such as well plates, in which a plurality of wells are formed using a plurality of nozzles are known (Japanese Patent No. 3413418, Japanese Patent No. 4962213, and Japanese Patent Laid-Open No. 2003-302411).

Among these, the device according to Japanese Patent No. 3413418 includes a plurality of nozzles in one array with distal ends thereof directed downward, a container inclination device for causing a container to be inclined is provided below the aligned nozzles, and a liquid is suctioned from storing portions corresponding to one array in a state in which the container is caused to be inclined.

Also, the device according to Japanese Patent No. 4962213 includes a plurality of nozzles in one array with distal ends thereof directed downward and includes a nozzle inclination device for causing the nozzles in one array to be integrally inclined in a direction that perpendicularly intersects an alignment direction, and a liquid is discharged to storing portions corresponding to one array in the container in a state in which the nozzles corresponding to the one array is caused to be inclined.

Moreover, the device according to Japanese Patent (Laid-Open) No. 2003-302411 includes a plurality of nozzles in a plurality of arrays with distal ends thereof directed downward, and a liquid is suctioned from storing portions corresponding to a plurality of arrays in a state in which a container is caused to be inclined, by causing the lengths of the nozzles in an array direction to be different from each other in accordance with differences in height of the storing portions in the array direction of the container supported in an inclined manner.

Here, both the devices according to Japanese Patent No. 3413418 and Japanese Patent (Laid-Open) No. 2003-302411 are configured to suction liquids using the plurality of nozzles from the plurality of storing portions in the containers formed by the plurality of aligned storing portions, and an object thereof is to suction the liquids without leaving the liquids by inclining the containers.

However, the device according to Japanese Patent No. 3413418 includes the nozzles in only one array, and it is necessary to perform the suctioning operation a plurality of times in accordance with the number of arrays for a container in which the storing portions are formed in a plurality of arrays, which is not efficient.

Also, although the device according to Japanese Patent (Laid-Open) No. 2003-302411 can suction the liquid from the storing portions aligned in a plurality of arrays at once, the container is supported in an inclined manner from the start of the suctioning, and the liquid may spill out when the nozzles are inserted depending on the storing amount of the liquid. Moreover, since the inclination angle of the container is fixed, and the lengths of the nozzles, which are different in the array direction, are fixed in accordance with the inclination angle of the container, a degree of freedom in movement of the nozzles inside the storing portions is low, and this leads to insufficient versatility.

On the other hand, although the device according to Japanese Patent No. 4962213 is configured to discharge a liquid to the plurality of storing portions in the container formed by the plurality of aligned storing portions using the plurality of nozzles, the device includes the nozzles in only one array similarly to Japanese Patent No. 3413418, which is not efficient.

In view of such problems, the present invention provides a liquid suction/discharge device that enables efficient suctioning and discharging of a liquid to a container formed by a plurality of aligned storing portions for storing the liquid, using a plurality of nozzles.

SUMMARY OF THE INVENTION

A liquid suction/discharge device includes a container support device for supporting a container formed by a plurality of aligned storing portions for storing a liquid; and a nozzle support device for supporting a plurality of nozzles aligned to correspond to the plurality of storing portions in a state in which distal ends of the nozzles are directed downward. The nozzle support device includes a nozzle support member that swingably supports the plurality of nozzles using a prescribed part of each of the nozzles as a support point, and the liquid suction/discharge device further includes a nozzle inclination device for causing each of the nozzles to be inclined with respect to the nozzle support member.

According to the invention, since the nozzle support member that swingably supports the plurality of nozzles using the prescribed part of each of the nozzles as a support point and the nozzle inclination device for causing each of the nozzles to be inclined with respect to the nozzle support member are included, it is possible to incline each nozzle itself in a prescribed orientation at the time of suctioning or discharging the liquid. It is also easy to provide the plurality of nozzles and to configure the nozzles to be individually inclined, and it is thus also possible to efficiently suction or discharge the liquid from or to the storing portions corresponding to a plurality of arrays.

DETAILED DESCRIPTION OF THE PREFERRED EMBODIMENT

Figure 1:
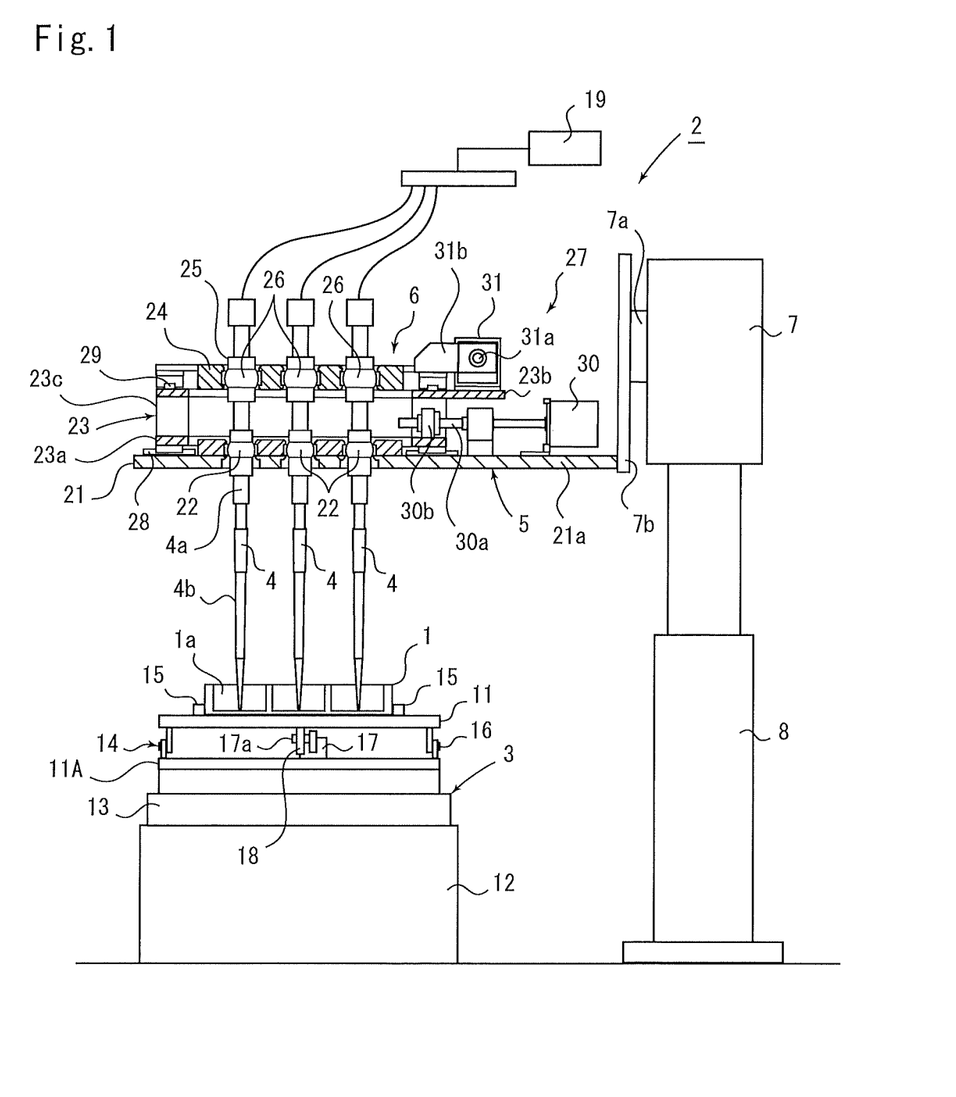
FIG. 1 is a side view of a liquid suction/discharge device according to an embodiment.

Hereinafter, an embodiment illustrated in the drawings will be described. FIG. 1 illustrates a liquid suction/discharge device 2 for suctioning and discharging a liquid from and to a culture container 1 that serves as a container.

Various operations are needed to culture cells these days, and for example, operations such as a culture liquid replacement operation for replacing a culture liquid, a passage operation for transferring the cells that are being cultured to other multiple culture containers 1, and a collecting operation for collecting the cells after the culture are accompanied by an operation including suctioning the liquid from the culture container 1 and discharging the suctioned liquid.

In the related art, such operations that are accompanied by suctioning and discharging of the liquid are manually performed by operators, and the operators suction and discharge the liquid with a distal end of a pipette located at a prescribed position in a petri dish while holding the pipette and the petri dish.

On the other hand, it has been necessary to culture a large number of cells for treatment and the like in recent years, and automatic suctioning and discharging of a liquid from and to the culture container 1 using the liquid suction/discharge device 2 as in the present embodiment is required to efficiently perform the culture.

The liquid suction/discharge device 2 according to the present embodiment is adapted to be able to suction and discharge a liquid to a culture container 1 in a sterile environment, and further, it is possible to perform other culture operations in parts that are adjacent to the liquid suction/discharge device 2 in the sterile environment.

Figure 2:
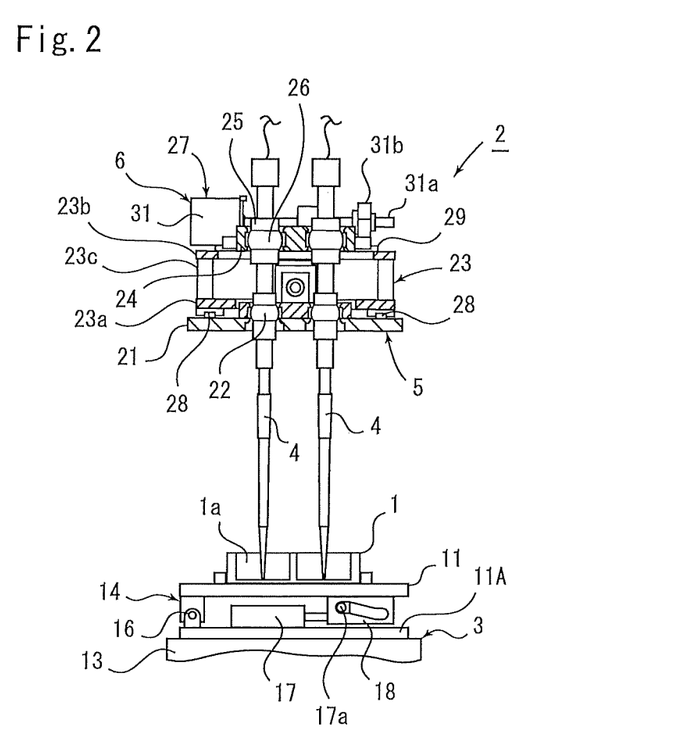
FIG. 2 is a front view of main parts of the liquid suction/discharge device.
Figure 3A:
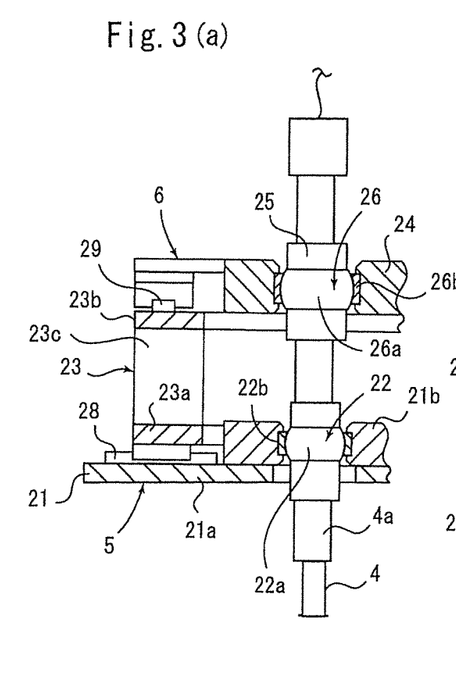
FIGS. 3(a) and 3(b) are enlarged views illustrating a nozzle inclination device.
Figure 3B:
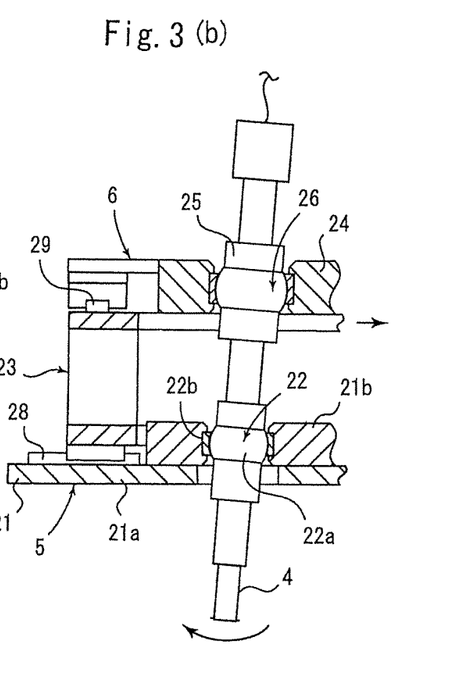
Figure 4:
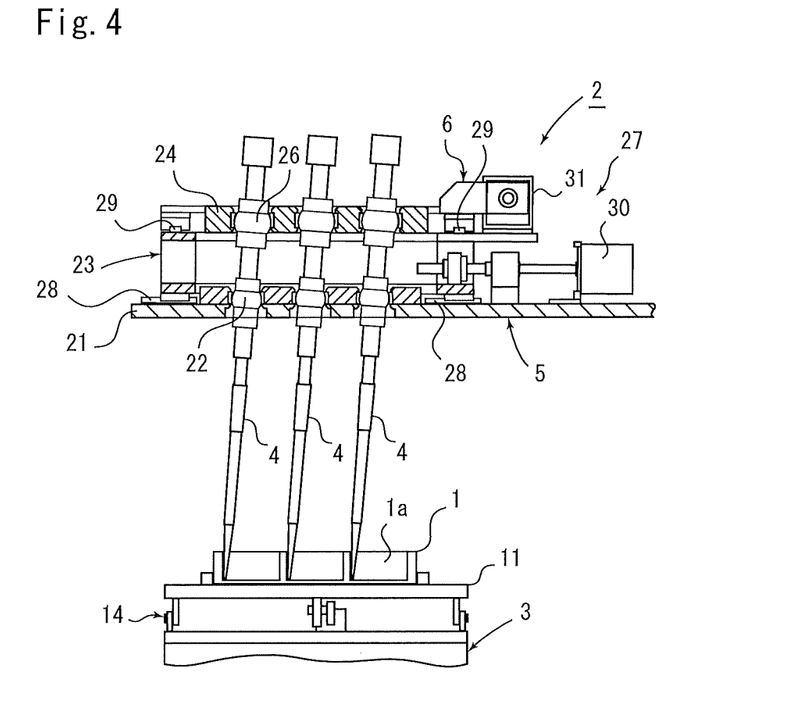
FIG. 4 is a side view of a state in which the nozzles are inclined.
Figure 5:
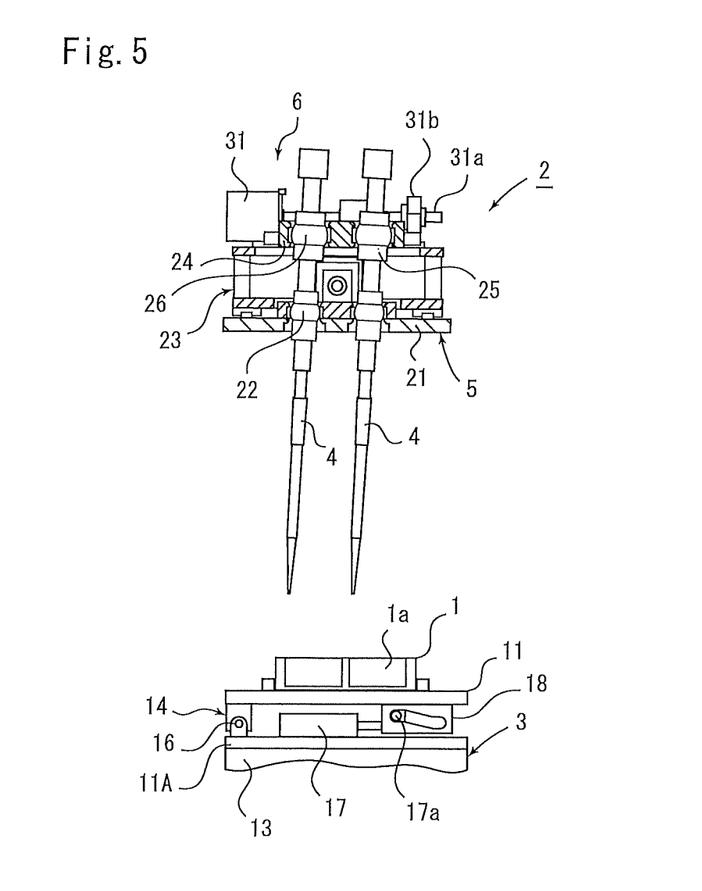
FIG. 5 is a front view of a state in which the nozzles are inclined.
Figure 6:
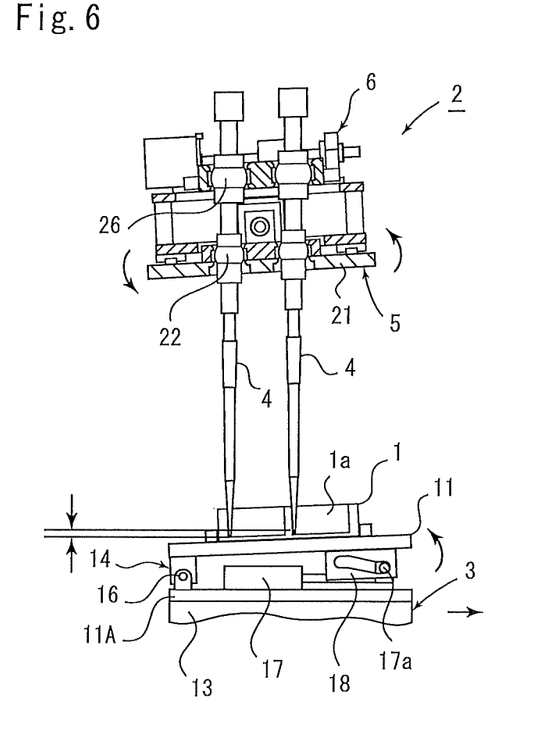
FIG. 6 is a front view of a state in which a nozzle support member and a culture container are inclined.

The liquid suction/discharge device 2 includes a container support device 3 for supporting the culture container 1, a nozzle support device 5 for supporting a plurality of nozzles 4 with distal ends thereof directed downward, a nozzle inclination device 6 for causing the nozzles 4 of the nozzle support device 5 to be inclined, an inclination device 7 for causing the nozzle support device 5 to be inclined, and a lifting/lowering device 8 for lifting and lowering the nozzle support device 5. These devices are adapted to be controlled by a control device, which is not illustrated. Here, FIGS. 1 and 2 illustrate a side view and a front view of a state in which the nozzles 4 are directed vertically downward, FIGS. 3(a) and 3(b) illustrate enlarged views for explaining the nozzle support device 5 and the nozzle inclination device 6, FIGS. 4 and 5 illustrate a side view and a front view of a state in which the nozzles 4 are inclined by the nozzle inclination device 6, and FIG. 6 illustrates a front view of a state in which the inclination device 7 inclines a nozzle support member 21 that supports the nozzles 4 and the culture container 1.

Also, the culture container 1 used in the present embodiment is a well plate that is known in the related art, and a plurality of storing portions 1a are formed in one culture container 1 in an aligned manner in a plurality of arrays. The culture container 1 according to the present embodiment includes three storing portions 1a formed in each of two arrays, that is, a total of six storing portions 1a, or includes two storing portions 1a formed in each of three arrays, that is, a total of six storing portions 1a.

The bottom surfaces of the storing portions 1a formed in the culture container 1 are flat, and vertical inner wall surfaces are formed to surround the flat bottom surfaces. The storing portions 1a with such a shape are suitable for culturing cells with a characteristic that the cells grow in a state in which the cells are in close contact with flat surfaces.

Note that a culture container with another configuration can be used as the culture container 1 and may be a culture container 1 with more storing portions 1a formed therein or a culture container 1 in which the bottom surfaces of the storing portions 1a are formed into a spherical shape.

The container support device 3 includes a plate-shaped container support member 11 that supports the culture container 1, a base unit 12 that is secured to a prescribed installation surface, a container moving device 13 for causing the container support member 11 to move, and a container inclination device 14 for causing the container support member 11 to be inclined.

The container support member 11 is provided with a positioning member 15 that positions the culture container 1 at a predetermined position, such that the culture container 1 is installed by a robot, which is not illustrated, or an operator.

The container moving device 13 comprises an X-Y table that is known in the related art and can cause the culture container 1 supported by the container support member 11 to move in the horizontal direction. Note that the container moving device 13 is not limited to the X-Y table and may be a transport device provided with an inclination function.

The container inclination device 14 comprises a hinge 16 that rotatably couples end portions of a fixed plate 11A, that is fixed to the container moving device 13, to the container support member 11 as illustrated in FIG. 2, an air cylinder 17 that includes a cam follower 17a at a distal end of a rod that moves forward and backward, and a cam 18 with a cam groove formed to be engaged with the cam follower 17a of the air cylinder 17.

In FIG. 2, the hinge 16 is provided at a left end portion in the drawing, which corresponds to one end side of the fixed plate 11A and the container support member 11, and the container support member 11 can thus be turned upward and downward with respect to the fixed plate 11A around the hinge 16 using the right end portion in the drawing, which corresponds to the other end side, as a swinging end.

The container support member 11 is formed into a rectangular shape in a plan view, the hinge 16 is provided at one side of the rectangle, which corresponds to the one end side, and serves as a rotation center, and the culture container 1 is supported such that arrays of three storing portions 1a are disposed in parallel with the side.

The air cylinder 17 is fixed to the fixed plate 11A so as to be directed in a direction that perpendicularly intersects the side on the one end side of the container support member 11 on which the hinge 16 is provided, and the air cylinder 17 is adapted to reciprocate the cam follower 17a in the horizontal direction by extending a rod in a direction away from the one end side.

The cam 18 is formed into a plate shape and is fixed to a lower surface of the container support member 11 so as to hang down in parallel with a forward/backward direction of the rod of the air cylinder 17, and the cam groove with which the cam follower 17a is engaged is formed along the forward/backward direction of the rod of the air cylinder 17. The cam groove has a downward inclination in the direction in which the rod of the air cylinder 17 extends.

With such a configuration, the container support member 11 is horizontal, and the culture container 1 is maintained to be horizontal, in a state in which the air cylinder 17 causes the rod to move backward and the cam follower 17*a* is moved to the one end side of the container support member 11 on which the hinge 16 is provided as illustrated in FIGS. 2 and 5.

Starting from the horizontal state described above, when the rod of the air cylinder 17 is caused to extend as illustrated in FIG. 6 and the cam follower 17*a* is moved away from the one end side of the container support member 11 on which the hinge 16 is provided, then the container support member 11 is pushed up via the cam 18 due to the movement of the cam follower 17*a* and is turned upward around the hinge 16, and inclination is achieved such that the one end side of the container support member 11 of the culture container 1 on which the hinge 16 is provided is placed at a lower position while the other side is placed at a higher position.

Each nozzle 4 comprises a tubular member 4*a* that is supported by the nozzle support device 5 and a tip 4*b* with a conical distal end provided at a lower end portion of the tubular member 4*a*, and the tip 4*b* can be replaced after use.

Also, in the present embodiment, three nozzles 4 in each of two arrays, or two nozzles 4 in each of three arrays, that is, a total of six nozzles 4 are provided and are aligned with the plurality of storing portions 1*a* formed in the culture container 1. Note that the number and alignment form of the nozzles 4 can be appropriately changed in accordance with the number and the alignment state of the storing portions 1*a* in the culture container 1, and it is also possible to align the nozzles 4 in one array instead of a plurality of arrays.

Although the state in which the plurality of storing portions 1*a* and nozzles 4 are aligned on straight lines are expressed as arrays, and the front-back direction of the straight lines is defined as an array direction in the above description, there may be a case in which description will be given on the assumption that the direction (left-right direction in FIG. 1) in which the three storing portions 1*a* illustrated in the section of the side view in FIG. 1 are aligned is the "array direction" and the direction (left-right direction in FIG. 2) in which the two storing portions 1*a* illustrated in the section of the front view in FIG. 2 are aligned is the "direction that perpendicularly intersects the array direction" as needed, and there may be a case in which a similar description will also be given for the alignment direction of the nozzles 4 corresponding to the storing portions 1*a*.

Each of the nozzles 4 is connected to a suctioning device 19 comprising a pump or the like, and it is possible to suction the same amount of liquid into each nozzle 4 by operating the suctioning device 19 and to discharge the liquid inside the nozzle 4 by discontinuing the suctioning.

The nozzle support device 5 is configured such that the distal ends of the nozzles 4 can move within a range of a recessed surface shape by swingably supporting the plurality of nozzles 4 using prescribed parts as support points with the distal ends directed downward.

As illustrated in FIGS. 1, 2, and 3, the nozzle support device 5 includes a plate-shaped nozzle support member 21 with a plurality of through-holes drilled in accordance with the positions of the aligned nozzles 4 and support point spherical bearings 22 that are provided in the through-holes of the nozzle support member 21 to swingably and axially support the nozzles 4 using the prescribed parts as support points.

The nozzle support member 21 according to the present embodiment comprises two plate-shaped members, the nozzle support member 21 is supported by the inclination device 7 by being coupled to a lower plate-shaped member 21*a* which is one of the two plate-shaped members. The nozzle support member 21 is kept horizontal by the inclination device 7 in an ordinary state as illustrated in FIGS. 2 and 5, while the nozzle support member 21 is caused to swing and is inclined as a whole as illustrated in FIG. 6 as needed.

The centers of the six through-holes drilled in the nozzle support member 21 are provided to conform to the centers of the storing portions 1*a* in the culture container 1 supported by the container support member 11, such that a center axis of each nozzle 4 vertically supported by the nozzle support member 21 conforms to the center of each storing portion 1*a* in the culture container 1.

The support point spherical bearings 22 are provided at the through-holes formed in an upper plate-shaped member 21*b* of the nozzle support member 21 and are included in the same plane in the nozzle support member 21.

Each support point spherical bearing 22 comprises an inner ring 22*a* that is attached to an outer periphery of the tubular member 4*a* of the nozzle 4 via a tubular element for fixation and an outer ring 22*b* fitted to the through-hole in the upper plate-shaped member 21*b*, and the inner ring 22*a* is freely turned in any direction inside the outer ring 22*b*.

With such a configuration, the nozzle 4 can swing using the center position of the inner ring 22*a* as a support point, the nozzle 4 is thus inclined, and the distal end portion of the nozzle 4 spaced from the support point moves within the range of the recessed surface shape.

The nozzle inclination device 6 comprises a moving frame 23 that is movably provided on an upper surface of the lower plate-shaped member 21*a* of the nozzle support member 21, a plate-shaped nozzle inclination member 24 that is movably provided on the upper surface of the moving frame 23, a sliding bearing 25 that slidably supports each nozzle 4, an inclination spherical bearing 26 that swingably and axially supports the sliding bearing 25, and a parallel movement device 27 that causes the nozzle inclination member 24 to move.

The moving frame 23 comprises a lower frame 23*a* and an upper frame 23*b* provided on upper and lower sides as illustrated in FIGS. 3(*a*) and 3(*b*) and a leg portion 23*c* provided between the lower frame 23*a* and the upper frame 23*b*, and the lower frame 23*a* and the upper frame 23*b* are provided to be parallel with each other.

Also, the lower frame 23*a* is disposed to surround the upper plate-shaped member 21*b*, and the upper frame 23*b* is disposed to surround all the nozzles 4 supported by the nozzle support member 21 to prevent interference.

Also, the upper surface of the lower plate-shaped member 21*a* of the nozzle support member 21 is provided with first rails 28 in an array direction including three nozzles 4, and the upper surface of the upper frame 23*b* is provided with second rails 29 in a direction that perpendicularly intersects the first rails 28.

The first rails 28 are disposed at four locations in the surroundings of the above plate-shaped member 21*b* to movably support the moving frame 23 with respect to the nozzle support member 21, and the second rails 29 are disposed on the front and back sides of the nozzles 4 in the array direction to movably support the nozzle inclination member 24 with respect to the nozzle support member 21 and the moving frame 23.

With such a configuration, the moving frame 23 and the nozzle inclination member 24 supported by the moving frame 23 can move in the array direction of the nozzles 4 along the first rails 28, and the nozzle inclination member 24 can move in the direction that perpendicularly intersects the array direction of the nozzles 4 along the second rails 29.

Also, the aforementioned configuration enables the nozzle inclination member 24 to move in parallel with the disposition plane of the plurality of support point spherical bearings 22 supported by the upper plate-shaped member 21b of the nozzle support member 21.

The nozzle inclination member 24 includes three through-holes in each of two arrays, that is, a total of six through-holes formed in accordance with the disposition of the nozzles 4 supported by the nozzle support member 21.

Thus, in a state in which the moving frame 23 is located at an intermediate position of the moving range provided by the first rails 28, and the nozzle inclination member 24 is located at the intermediate position of the moving range provided by the second rails 29, each nozzle 4 supported by the nozzle support member 21 is located at the center of the corresponding through-hole in the nozzle inclination member 24 and is maintained vertically.

Each through-hole in the nozzle inclination member 24 is provided with a sliding bearing 25 via the inclination spherical bearing 26, and the tubular member 4a of each nozzle 4 that corresponds to the position of each through-hole and is supported by the nozzle support member 21 is slidably supported by the corresponding sliding bearing 25.

Each inclination spherical bearing 26 comprises an inner ring 26a that is attached to an outer periphery of the sliding bearing 25 and an outer ring 26b that is fitted to the inside of the through-hole in the nozzle inclination member 24, and the inner ring 26a is freely turned in any direction inside the outer ring 26b.

With such a configuration, each inclination spherical bearing 26 and each sliding bearing 25 are disposed in the same plane by being supported by the nozzle inclination member 24 and press each nozzle 4 in the horizontal direction via the sliding bearing 25 as illustrated in FIG. 3(b) by causing the nozzle inclination member 24 to move in parallel with the nozzle support member 21.

When the nozzle 4 is pressed in parallel with the nozzle support member 21, then the pressed part serves as a point of action, the turning center part of the support point spherical bearing 22 in the nozzle 4 supported by the nozzle support member 21 serves as a support point, the distal end of the nozzle 4 swings in the direction opposite to the moving direction of the nozzle inclination member 24, and each nozzle 4 is brought into an inclined state in the same direction.

Here, although the nozzle inclination member 24 presses the part that serves as the point of action of the nozzle 4, which swings around the support point spherical bearing 22, in a tangential direction, it is possible to smoothly incline the nozzle 4 while causing the nozzle 4 to slide relative to the sliding bearing 25 by supporting each nozzle 4 via the sliding bearing 25.

Also, since the positional relationship of the plurality of through-holes in the nozzle inclination member 24 and the positional relationship of the plurality of through-holes in the nozzle support member 21 do not change, it is possible to cause all of the nozzles 4 supported by the nozzle support device 5 to be inclined in the same direction in unison using the nozzle inclination device 6.

The parallel movement device 27 comprises the first rails 28 that are provided on the lower plate-shaped member 21a of the nozzle support member 21 to guide the movement of the moving frame 23, a first motor 30 that causes the moving frame 23 to move along the first rails 28, the second rails 29 that are provided on the upper frame 23b of the moving frame 23 to guide the movement of the nozzle inclination member 24, and a second motor 31 that causes the nozzle inclination member 24 to move along the second rails 29.

The first motor 30 is fixed to the upper surface of the lower plate-shaped member 21a of the nozzle support member 21 and drives and rotates a screw shaft 30a disposed in parallel with the first rails 28, and the lower frame 23a of the moving frame 23 is provided with a nut member 30b that is screwed onto the screw shaft 30a.

On the other hand, the second motor 31 is fixed to the upper surface of the upper frame 23b of the moving frame 23 and drives and rotates a screw shaft 31a disposed in parallel with the second rails 29, and the nozzle inclination member 24 is provided with a nut member 31b that is screwed onto the screw shaft 31a.

With such a configuration, it is possible to cause the nozzle inclination member 24 to move on the front and back sides of the nozzles 4 in the array direction by causing the moving frame 23 to move forward and backward using the first motor 30, and it is possible to cause the nozzle inclination member 24 to move on the front and back sides in the direction that perpendicularly intersects the array direction of the nozzles 4 by causing the nozzle inclination member 24 to move forward and backward using the second motor 31. It is thus possible to cause each nozzle 4 to be inclined at the same time toward the array direction in which the nozzles 4 are aligned or the direction that perpendicularly intersects the array direction.

In addition, it is possible to cause the nozzle inclination member 24 to move in a two-dimensional composite direction by causing the first motor 30 and the second motor 31 to work in conjunction with one another and thereby to cause the distal end of each nozzle 4 to move not only in a linear manner but also in a circular or a curved trajectory.

The inclination device 7 includes a drive shaft 7a that is driven and rotated by a servo motor, which is not illustrated, and is horizontally disposed and a swinging member 7b that is attached to the drive shaft 7a, and the lower plate-shaped member 21a of the nozzle support member 21 is horizontally coupled to and supported by the swinging member 7b.

It is thus possible to cause the nozzle support member 21 and the nozzle inclination member 24 to reciprocate in an arc trajectory that perpendicularly intersects the array direction of the nozzles 4 around the drive shaft 7a by causing the drive shaft 7a to be turned in forward and backward directions and to cause the plurality of nozzles 4 to be integrally inclined along with the nozzle support member 21.

The lifting/lowering device 8 is adapted to be driven by an actuator such as a motor or a drive cylinder, which is not illustrated, and to lift and lower the inclination device 7, and thus cause the nozzle support member 21 and the nozzle inclination member 24 to move upward and downward, and is adapted to integrally lift and lower the plurality of nozzles 4 along with the nozzle support member 21.

Hereinafter, operations of the liquid suction/discharge device 2 with the aforementioned configuration will be described. As an example, operations performed when cells cultured in the culture container 1 are collected will be described.

The cells have grown in a state in which the cells adhere to the bottoms of the storing portions 1a, and in order to collect the cells, it is necessary to perform an operation of discharging a liquid to surroundings of the adhering cells first to cause the cells to peel off and an operation of suctioning and collecting the cultured liquid in which cells that have peeled off are floating.

First, the operation performed when the cells adhering to the bottom of each storing portion 1a in the culture container 1 are peeled off will be described. Note that the following operations are registered in the control device in advance so as to be automatically performed.

The nozzle support member 21 has been retreated upward by the lifting/lowering device 8 when the culture container 1 storing cells is set in the liquid suction/discharge device 2, and if the culture container 1 is set at a prescribed position in the container support member 11 by the positioning member 15, then the lifting/lowering device 8 lowers the nozzle support member 21 via the inclination device 7 as illustrated in FIGS. 1 and 2, and the distal end of each nozzle 4 is inserted into each storing portion 1a in the culture container 1.

In order to prevent the cells stored in the storing portions 1a from being damaged at this time, the amount of lowering achieved by the lifting/lowering device 8 is adjusted such that the distal ends of the nozzles 4 are stopped at positions at which the distal ends are spaced upward from the bottom surfaces of the storing portions 1a and are also dipped in the culture liquid.

Then, the suctioning device 19 is caused to operate to suction a predetermined amount of culture liquid into each nozzle 4, thereby storing substantially the entire amount of culture liquid, which has been stored in each storing portion 1a, in each nozzle 4.

Thereafter, the parallel movement device 27 of the nozzle inclination device 6 operates to cause the moving frame 23 and the nozzle inclination member 24 to move in the array direction of the nozzles 4 through driving of the first motor 30, and the nozzles 4 are caused to be inclined in the array direction such that the distal end of each nozzle 4 is directed to the peripheral edge of the bottom surface as illustrated in FIG. 4.

Note that in the example in FIG. 4, the moving frame 23 and the nozzle inclination member 24 are caused to move by predetermined amounts toward the first motor 30, such that the upper portion above the support point of each nozzle 4 is inclined on the side of the first motor 30 to direct the distal end of the nozzle 4 in the direction opposite to the upper portion.

The first and second motors 30 and 31 are further caused to work in conjunction with one another from this state to cause the moving frame 23 to reciprocate by a predetermined distance in the array direction of the nozzles 4 through driving of the first motor 30 and to cause the nozzle inclination member 24 to reciprocate by a predetermined distance in a direction that perpendicularly intersects the array direction of the nozzles 4 through driving of the second motor 31.

It is possible to cause the nozzle inclination member 24 to move in a circular trajectory through such composite operations, and by the container moving device 13 additionally causing the culture container 1 to move in a revolving manner, each nozzle 4 is inclined using the part supported by the nozzle support member 21 as a support point, and the distal end of each nozzle 4 moves in a circular trajectory along the inner periphery of each storing portion 1a.

The movement trajectories of the nozzle inclination member 24 and the container support member 11 are registered in the control device such that the circular trajectories of the distal ends of the nozzles 4 circularly move along the outer peripheral edges of the bottom surfaces of the storing portions 1a in the culture container 1.

The culture liquid that has been suctioned into the nozzles 4 is caused to be discharged by releasing the suctioning achieved by the suctioning device 19 while causing the distal end of each nozzle 4 to move along the outer peripheral edge of the bottom surface of the storing portion 1a in this manner, and the cells adhering to the bottom surface of the storing portion 1a are caused to peel off.

Such an operation of causing the distal end portions of the nozzles 4 to move along the peripheral edges of the bottom surfaces of the storing portions 1a while causing the nozzles 4 to be inclined reproduces an actual operation performed by an operator, it is advantageously possible to perform the process on all the storing portions 1a aligned in a plurality of arrays at the same time according to the liquid suction/discharge device 2 of the present invention, as compared to the process which has to be performed on the storing portions 1a one by one in the case where the operator performs the process.

Next, operations performed when cells after culture are suctioned from the culture container 1 using the liquid suction/discharge device 2 will be described. At this time, the cells that have been cultured in the culture container 1 have been peeled off from the bottom surface of each storing portion 1a and are floating in the culture liquid.

First, the distal ends are kept above the bottom surfaces of the storing portions 1a and are still dipped in the culture liquid in a state in which each nozzle 4 is vertically maintained as illustrated in FIG. 2, the suctioning device 19 is caused to operate in that state to suction the culture liquid containing a predetermined amount of cells into each nozzle 4, and the culture liquid containing substantially almost all of the cells is thus stored in each nozzle 4.

However, since the culture liquid containing cells still remains in each storing portion 1a, there is a need to suction the remaining culture liquid as well into each nozzle 4.

Thus, the lifting/lowering device 8 causes the nozzle support member 21 to be lifted to position each nozzle 4 above each storing portion 1a once as illustrated in FIG. 5 from the above state, and the second motor 31 of the parallel movement device 27 configuring the nozzle inclination device 6 is then caused to operate to cause the nozzle inclination member 24 to move by a predetermined amount in a direction away from the second motor 31.

In this manner, the upper portion of each nozzle 4 above the support point is caused to be inclined in a direction away from the second motor 31, which is a direction that perpendicularly intersects the array direction of the nozzles 4, and the distal end of each nozzle 4 is directed in the direction opposite to the upper portion.

Thereafter, the inclination device 7 causes the nozzle support member 21 to be inclined in a direction that is opposite to the direction in which each nozzle 4 was previously inclined and that perpendicularly intersects the array direction of the nozzles 4 such that the posture of each supported nozzle 4 is substantially vertical as illustrated in FIG. 6.

On the other hand, the air cylinder 17 of the container inclination device 14 is caused to operate in the container support member 11 supporting the culture container 1, the piston rod is caused to extend to cause the cam follower 17a to move in a direction away from the air cylinder 17, and the culture container 1 is caused to be inclined along with the container support member 11.

In other words, the inclination direction of the container support member 11 in this case is the same direction as the direction in which the nozzle support member 21 is caused to be inclined to keep each nozzle 4 vertical.

In this manner, the culture container 1 is inclined to be lowered toward the direction of the hinge 16 as illustrated in FIG. 6, and in this state, each storing portion 1a is brought into a state in which the storing portion 1a is inclined in a direction that perpendicularly intersects the array direction with the array on the side near the hinge 16 located at a lower position and with the array on the farther side located at a higher position.

As a result, in each storing portion 1a in the inclined culture container 1, the culture liquid containing cells is gathered at a lowest part of the storing portion 1a.

Also, the container moving device 13 is caused to operate at the same time with causing the container support member 11 to be inclined, and the container support member 11 is caused to move in the same direction as the moving direction of the distal end of each nozzle 4 when the inclination device 7 causes the nozzle support member 21 to be inclined to keep each nozzle 4 vertical. In this manner, the lowest part of each storing portion 1a is located below the distal end of each nozzle 4 in a vertical posture above the culture container 1, and relative positioning between the distal end of each nozzle 4 and each corresponding storing portion 1a is performed.

In a state in which such positioning has been performed, the lifting/lowering device 8 is caused to operate to cause each nozzle 4 to be lowered along with the nozzle support member 21 in an inclined state and cause the distal end of the corresponding nozzle 4 to approach the lowest part of each storing portion 1a in the inclined culture container 1, and the suctioning device 19 is caused to operate in this state to suction the culture liquid containing the remaining cells and to suction the entire liquid in each storing portion 1a.

The operation of suctioning the liquid in a state in which the culture container 1 is caused to be inclined and the distal ends of the nozzles 4 are caused to be located at the lowest part in the storing portions 1a in this manner also reproduces an actual operation of an operator, it is also advantageously possible to perform the process on all the storing portions 1a aligned in a plurality of arrays as targets according to the liquid suction/discharge device of the present invention, as compared to the process which has to be performed on the storing portions 1a one by one in the case where the operator performs the process.

Since each of the plurality of nozzles 4 is swingably supported by the nozzle support member 21 and is able to be inclined in the present invention, in particular, it is possible to cause each of the nozzles 4 to be inclined with the distal ends having the same heights in the same direction, with respect to the plurality of storing portions 1a aligned in the array direction in the culture container 1 supported by the horizontal container support member 11 as illustrated in FIG. 4, for example.

In this manner, it is possible to cause all of the nozzles 4 aligned in the plurality of arrays to be similarly inclined with the distal ends having the same heights and to discharge the liquid into all the storing portions 1a at the same time.

Moreover, it is possible to cause the plurality of nozzles 4 aligned in the array direction (the direction of the arrays in the direction that perpendicularly intersects the array direction in the present embodiment) relative to the plurality of storing portions 1a aligned in the direction in which the culture container 1 supported by the inclined container support member 11 is inclined to be inclined relative to the nozzle support member 21 such that the distal ends are directed in the direction in which the inclined container support member 11 is lowered, and also, it is possible to cause the nozzle support member 21 to be inclined in the same direction as the direction of the container support member 11 using the inclination device 7, as illustrated in FIG. 6.

In this manner, it is possible to direct the distal ends of the corresponding nozzles 4 aligned in the array direction to the lowest parts of the bottom surfaces of the storing portions 1a inclined with different heights in the array direction and to suction the liquid from all the storing portions 1a at the same time.

As described above, according to the liquid suction/discharge device 2 in the present embodiment, the nozzle support device 5 swingably and axially supports each of the plurality of nozzles 4, and it is thus possible to cause the distal end of each nozzle 4 to move within the range of the recessed surface shape and to reproduce the complicated operations performed by the operator.

Here, the aforementioned operations are just an example, and the liquid suction/discharge device 2 in the present embodiment can reproduce various operations that are performed by various organizations through prior registration of the operations in the control device.

Also, since the plurality of nozzles 4 are supported by the nozzle support device 5, it is possible to perform the aforementioned complicated operations on the plurality of storing portions 1a in the culture container 1 at the same time.

Note that in the embodiment, the nozzle support device 5 swingably supports the nozzles 4 using the prescribed parts as support points and the nozzles 4 are caused to be inclined by the nozzle inclination device 6 pressing the parts above the support points as points of action.

On the other hand, the parts to be pressed as the points of action may be parts below the support points, or further, the support point spherical bearings 22 in the nozzle support device 5 may be driven and rotated by an actuator such as a motor or an air cylinder or prescribed driving device using non-contact power such as a magnetic force, for example, without pressing the points of action.

In this manner, it is possible to configure the driving device as the nozzle inclination device 6 adapted to directly cause the support point parts to rotate and cause the nozzles 4 to swing.

What is claimed is:

1. A liquid suction and discharge system for suctioning liquid from, and discharging liquid to, a container including a plurality of liquid storing portions aligned in a plurality of arrays, the liquid suction and discharge system comprising:
   a plurality of nozzles arranged to be positioned relative to the plurality of liquid storing portions of the container aligned in a plurality of arrays;
   a container support device for supporting the container;
   a nozzle support device supporting the plurality of nozzles in a state in which distal ends of the plurality of nozzles are directed downward and aligned in at least one array;
   a suction device configured for suctioning liquid from the plurality of liquid storing portions of the container by applying suction to the plurality of nozzles, and configured for discharging liquid from the plurality of nozzles by releasing the suction applied to the plurality of nozzles; and
   an elevation device supporting the nozzle support device in an elevatable manner above the container support device;
   the nozzle support device comprising a plate-shaped nozzle support member;
   the plate-shaped nozzle support member including drilled through holes in at least one array, the through holes being respectively provided with spherical bearings so that the plurality of nozzles are swingably supported by the spherical bearings using a first part of each nozzle of the plurality of nozzles as a support point;

a moving frame on an upper surface of the plate-shaped nozzle support member and a plate-shaped nozzle inclination member on an upper surface of the moving frame, the moving frame surrounding each nozzle of the plurality of nozzles supported by the nozzle support member and provided so as to be movable in a same direction as or a direction perpendicularly intersecting an array direction of each nozzle of the plurality of nozzles, and the plate-shaped nozzle inclination member is provided in a direction perpendicularly intersecting a direction in which the moving frame is movable;

the plate-shaped nozzle inclination member including a plurality of drilled through holes in an arrangement corresponding to the plurality of nozzles supported by the nozzle support member, and each through hole of the plurality of through holes of the nozzle inclination member is provided with a sliding bearing such that a second part that is separated upward from the first part of each nozzle of the plurality of nozzles by a predetermined distance is slidably supported by the sliding bearing; and a first motor configured to move the moving frame on the plate-shaped nozzle support member and a second motor configured to move the plate-shaped nozzle inclination member on the moving frame in a direction perpendicularly intersecting a moving direction of the moving frame, such that the moving frame and the nozzle inclination member are moved to incline the plurality of nozzles supported by the nozzle support member in unison with one another.

\* \* \* \* \*